United States Patent [19]

Kopineck et al.

[11] 4,337,662
[45] Jul. 6, 1982

[54] ELECTRODYNAMIC SOUND CONVERTER

[75] Inventors: Hermann J. Kopineck, Dortmund; Wolfgang Böttcher, Schwerte; Klaus D. Mreyen, Holzwickede; Werner Borchert, Bochum; Volker Deutsch, Wuppertal, all of Fed. Rep. of Germany

[73] Assignee: Estel Hoesch Werke AG, Dortmund, Fed. Rep. of Germany

[21] Appl. No.: 208,820

[22] Filed: Nov. 20, 1980

[30] Foreign Application Priority Data

Dec. 7, 1979 [DE] Fed. Rep. of Germany ....... 2949256

[51] Int. Cl.³ ............................................. G01N 29/04
[52] U.S. Cl. ...................................... 73/632; 324/262
[58] Field of Search ................. 73/632, 633, 635, 644; 324/262; 310/322, 323, 334, 336

[56] References Cited

U.S. PATENT DOCUMENTS 4,258,319  3/1981  Shimada et al. .................... 324/262
4,314,203  2/1982  Häberlein ............................ 324/262

FOREIGN PATENT DOCUMENTS 596917  3/1978  U.S.S.R. ................................ 73/632

Primary Examiner—Stephen A. Kreitman
Attorney, Agent, or Firm—Max Fogiel

[57] ABSTRACT

An electrodynamic sound converter is disclosed for the non-destructive ultrasonic testing of workpieces during relative movement of the workpiece and the testing head. The testing head has an annular electromagnet which produces a magnetic field, and a rod-shaped core extends coaxially through the electromagnet and has a tip which projects beyond the same in direction towards the workpiece to be tested. The core is axially slidable relative to the electromagnet towards and away from the workpiece and the electromagnet and the tip of the core are each independently maintained at a fixed predetermined spacing from a surface of the workpiece being tested. The tip is being biased towards the surface, and a high-frequency coil is located adjacent the tip and serves to produce electromagnetic oscillations. Various modifications are also disclosed.

10 Claims, 1 Drawing Figure

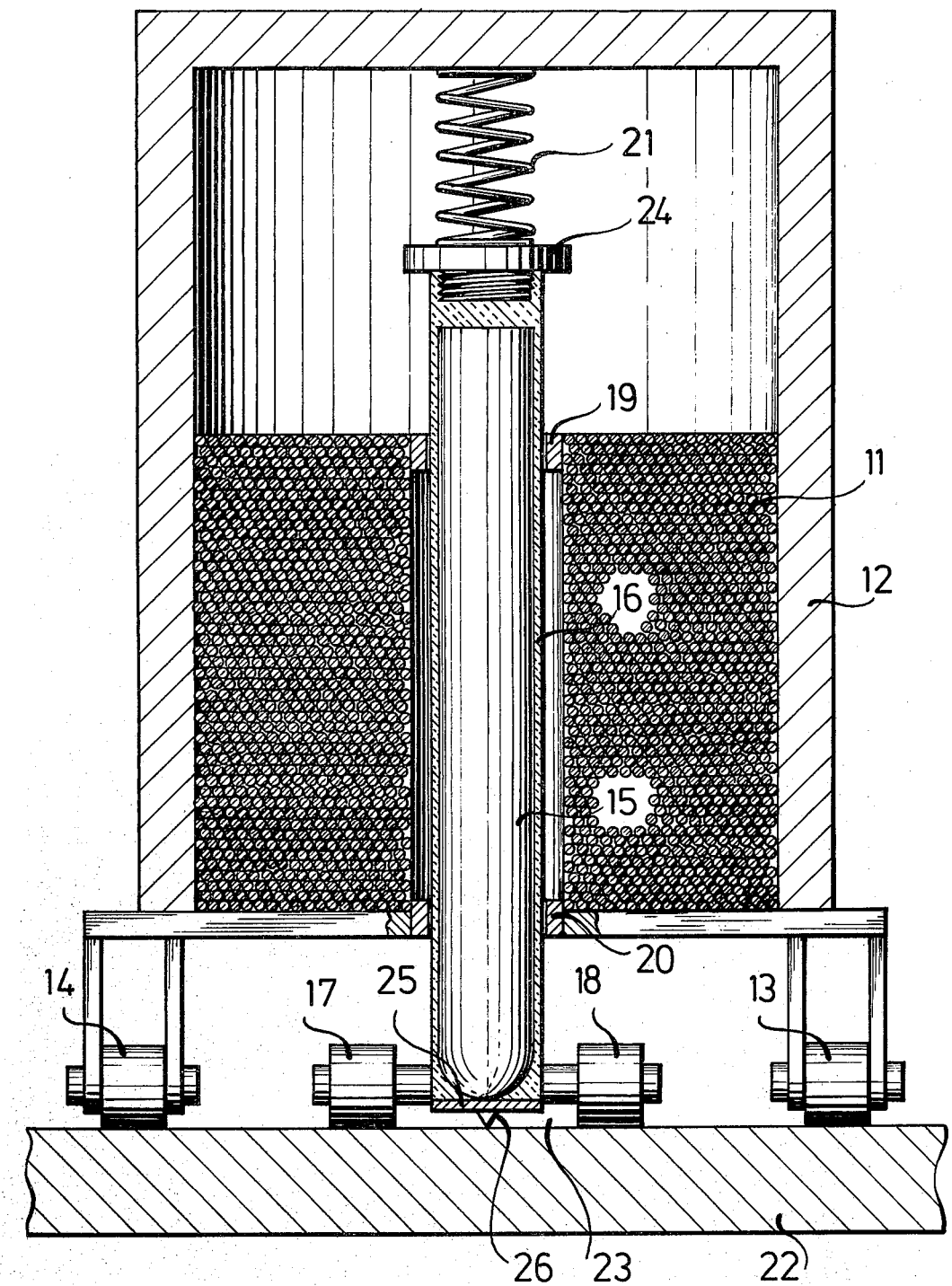

ELECTRODYNAMIC SOUND CONVERTER

BACKGROUND OF THE INVENTION

The present invention relates to an electrodynamic sound converter, and more particularly to an electrodynamic sound converter for use in the non-destructive ultrasonic testing of workpieces by means of relative movement of the workpiece and of the testing head, respectively.

Equipment of this general type is known, and during the testing the testing head of the ultrasonic flaw detector is moved along the workpiece surface and/or the workpiece surfaces moved relative to the testing head. In order to obtain exact test results it is necessary that a small air gap be maintained between the testing head and the workpiece, and that this air gap be as constant as possible. Problems are encountered during this type of testing if the workpiece surface is uneven. It is known to support the entire testing head on rollers which roll along the workpiece surface and this is a viable solution so long as the relative movement between testing head and workpiece is comparatively slow, because the unevenness of the workpiece surface can be compensated with this arrangement and the air gap can be maintained constant or substantially so. The same is not true, however, if the workpiece and the testing head are displaced at high relative speeds, or if the workpiece surface has unevennesses which follow one another very closely. The problem is that in either of those possibilities the rollers supporting the testing head on the workpiece surface in effect jump from high point to high point of the workpiece surface and the overall testing head—which has a relatively high inertia due to its mass—requires too much time to accommodate itself sufficiently to the depressions so as to maintain a uniform air gap.

Another problem which is independent of the speed of the relative movement is encountered in the prior art if the workpiece surface has closely adjacent unevennesses (i.e. depressions and projections) and if the distance of the spacing members (i.e. rolls or the like) from one another as seen in the direction of relative movement is of the same order of magnitude as the length of the unevennesses. Here, again, the desired constancy of the air gap between the testing head and the workpiece surface cannot be maintained.

SUMMARY OF THE INVENTION

Accordingly, it is a general object of the invention to overcome the disadvantages of the prior art as outlined above.

A more particular object of the invention is to provide an improved arrangement for the non-destructive ultrasonic testing of workpieces of the general type under discussion, but which is able to maintain the desired constant air gap between testing head and workpiece even though the workpiece surface is provided with closely adjacent unevennesses, and independently of the relative speed of movement of testing head and workpiece surface.

Another object of the invention is to provide such an arrangement which is capable of maintaining the constancy of the air gap even if the distance of the spacing members which maintain the testing head spaced from the workpiece surface is, as considered in the direction of relative movement, of the same order of magnitude as the length of the unevennesses.

In keeping with the above objects, and with still others which will become apparent hereafter, one feature of the invention resides in an electrodynamic sound converter for non-destructive ultrasonic testing of workpieces during relative movement of the workpiece and the testing head. Briefly stated, such a converter may comprise an annular electromagnet operative for producing a magnetic field, a rod-shaped core extending coaxially through the electromagnet and having a tip projecting beyond the same in direction towards a workpiece to be treated, and means mounting the core to be axially slidable relative to the electromagnet, towards and away from the workpiece.

In addition, the arrangement will comprise means for independently maintaining the electromagnet and the tip of the core at fixed predetermined spacing from a surface of the workpiece, means for biasing the tip towards the work surface, and a high-frequency coil adjacent the tip and operative for producing electromagnetic oscillations.

An embodiment of the invention will hereafter be described with reference to the appended drawings. It is to be understood, however, that this is merely by way of example and that the scope of the protection sought for the invention is defined exclusively in the claims.

BRIEF DESCRIPTION OF THE DRAWING

The single FIGURE is a somewhat diagrammatic sectional elevation through an arrangement according to the invention and a portion of a workpiece being tested.

DESCRIPTION OF PREFERRED EMBODIMENTS

Referring now to the FIGURE in detail it will be seen that the electrodynamic sound converter according to the present invention includes a large-dimensioned electromagnet 11 the coil of which is mounted in the housing 12 thereof. The housing 12 includes rollers 13 and 14 which supported on the surface of the workpiece 22 to be tested, in such a manner that an air gap 23 remains between the workpiece 22 and an elongated core 15 which extends coaxially through the coil and housing of the electromagnet.

The core 15 is slidably guided in the coil of the electromagnet 11, so that it can move axially of itself, by means of guides 19 and 20. The core may be guided directly in the guides 19 and 20 or, as illustrated in the FIGURE, it may be accommodated in its own housing 16 which here is configurated in form of a sleeve. If a housing 16 is provided, it is composed of a non-magnetic material. The housing 16 is supported relative to the workpiece 22 by means of additional spacing rollers 17 and 18 and is pressed towards the workpiece by magnetic attracting forces existing between the core 15 and the workpiece 22; these forces of a magnitude which is in excess of ten times the gravitational weight of the core 15. If desired, this pressure can be supplemented by an expansion spring 21 which reacts between the housing 12 and a plug 24 which is inserted into the upper open end of the housing 16. Under other circumstances, where the pressure due to the magnetic forces is too high, it can be weakened by replacing the expansion spring 21 with a tension spring, i.e. a spring which tends to contract and against which the magnetic force must pull.

It will be appreciated that the rolls 17 and 18, as well as the rolls 13 and 14, may be replaced by other spacing elements, for example glide shoes or the like. In addition to, or in lieu of the rolls 17 and 18 the core 15 may be provided with a glide shoe or a small ball 26 which is located at its tip (it will be noted that the front end portion of the core 15 tapers towards the workpiece 22) and precisely situated on the longitudinal axis of the core 15, as illustrated.

When the entire testing head is lifted off the workpiece 22, the projecting outer edge of the plug 24 abuts the upper edge of the guide 19 so that the housing 16 is prevented from sliding out of the coil of the electromagnet 11.

Also located at the front end or tip of the core 15 is a small, flat high frequency coil 25 which is adhesively bonded or otherwise connected to the planar end face of the sleeve-shaped housing 16 for the core 15.

By thus having the core 15 mounted for axial movement relative to and independently of the electromagnet 11, and by having it maintained at permanent spacing from the workpiece surface independently of the spacing of the housing of the electromagnet 11, and further by biasing the core towards the surface of the workpiece 22, the problems inherent in the prior art are overcome and the device according to the present invention is capable of performing accurate measurement of a workpiece at high relative speed of workpiece and testing head, and even though unevennesses of the workpiece surface (these are not shown) are closely adjacent one another and the spacing between the rolls 13, 14 is on the order of the length of the unevennesses. This is further enhanced by the fact that advantageously the distance between the rollers 17, 18 of core 15 and the longitudinal central axis of core 15 (or, of course, of the member 26 and the longitudinal axis) is smaller than the distance between the rollers 13, 14 of the electromagnet 11 and the longitudinal axis of the core 15.

The invention has herein been described with reference to an exemplary embodiment. It will be understood, however, that it is receptable of various modifications which will offer themselves to those skilled in the art and which are intended to be encompassed within the protection sought for the invention, as set forth in the appended claims.

What is claimed is:

1. Electrodynamic sound converter for non-destructive ultrasonic testing of workpieces during relative movement of the workpiece and the testing head, comprising an annular electromagnet operative for producing a magnetic field; a rod-shaped core extending coaxially through said electromagnet and having a tip projecting beyond the same in direction towards a workpiece to be tested; means mounting said core to be axially slidable relative to said electromagnet, towards and away from the workpiece; means for independently maintaining said electromagnet and said tip of said core at fixed predetermined spacing from a surface of the workpiece; means for biasing said tip towards said surface; and a high-frequency coil adjacent said tip and operative for producing electromagnetic oscillations.

2. A converter as defined in claim 1, said electromagnet being slidable towards and away from the workpiece, and said maintaining means comprising spacing elements on said electromagnet and in contact with said surface of the workpiece.

3. A converter as defined in claim 2, said spacing elements being rollers.

4. A converter as defined in claim 2, said spacing elements being glide shoes.

5. A converter as defined in claim 1, said maintaining means comprising at least one spacer member.

6. A converter as defined in claim 5, said core having a central longitudinal axis and said axis and said spacer member being spaced from one another by a distance which is smaller than a similar distance between a spacer member of said electromagnet and said axis of said core.

7. A converter as defined in claim 1, said core having a longitudinal axis, and said maintaining means comprising a spacing element located at said tip and positioned on said longitudinal axis.

8. A converter as defined in claim 1, said tip converging in direction away from said electromagnet, further including a core housing surrounding said core, said high-frequency coil being connected to a planar end face of said housing.

9. A converter as defined in claim 1, said biasing means being constituted by said electromagnet.

10. A converter as defined in claim 1, said biasing means being a biasing spring.

* * * * *